United States Patent [19]
Kaiya et al.

[11] Patent Number: 6,165,481
[45] Date of Patent: Dec. 26, 2000

[54] HIGHLY PURE SQUALANE, RAW MATERIAL FOR PHARMACEUTICALS AND COSMETICS PREPARED BY USING THE SAME AND METHOD FOR PRODUCING THE SAME

[75] Inventors: Atsushi Kaiya; Tomio Nakamura, both of Kawasaki; Hironaka Wada, Sagamihara, all of Japan

[73] Assignee: Nippon Petrochemicals Company, Inc., Tokyo, Japan

[21] Appl. No.: 09/218,458

[22] Filed: Dec. 22, 1998

[30] Foreign Application Priority Data

Dec. 25, 1997 [JP] Japan .................................. 9-367433
Apr. 1, 1998 [JP] Japan .................................. 10-105795

[51] Int. Cl.⁷ ............................. A61K 6/00; A61K 9/00
[52] U.S. Cl. ................................................ 424/401
[58] Field of Search ............................................. 424/401

[56] References Cited

U.S. PATENT DOCUMENTS 3,304,263  2/1967  Yoke III et al. .
4,032,588  6/1977  Tomita et al. ...................... 260/676 R
5,718,904  2/1998  Hjorth .

FOREIGN PATENT DOCUMENTS 0 399 843 A2  11/1990  European Pat. Off. .
7-309785      11/1995  Japan .
9-140790      6/1997   Japan .
9-164162      6/1997   Japan .
367433        12/1997  Japan .

*Primary Examiner*—Carlos A. Azpuru
*Attorney, Agent, or Firm*—Hollander Law Firm, P.L.C.

[57] ABSTRACT

Highly pure squalane in which the content of pristane is reduced to 10 wt ppm or less, can be obtained by refining the squalane of animal oil or fat origin through thin film distillation, said highly pure squalane is useful as a raw material for producing cosmetics and medical and pharmaceutical preparations and especially, it is quite effective as a lubricating agent for condoms and as a component of adjuvant composition.

18 Claims, No Drawings

HIGHLY PURE SQUALANE, RAW MATERIAL FOR PHARMACEUTICALS AND COSMETICS PREPARED BY USING THE SAME AND METHOD FOR PRODUCING THE SAME

BACKGROUND OF THE INVENTION (1) Field of the Invention

This invention relates to highly pure squalane from shark-liver oil, which squalane is excellent in stability and scarcely contains pristane being stimulative to the skin. The invention further relates to the raw material of medical, pharmaceutical and cosmetic products using the same and a method for preparing the same.

(2) Prior Art

The squalane is represented by the following structural formula. It is excellent in the adaptivity to living bodies, good spreading property and safety in use, so that it is widely used for preparing almost all of cosmetics such as several kinds of creams, especially nutrient cream and medicated creams, milky lotion, toilet lotion, lipstick, foundation, and face powder. In addition, it is used as a fatting agent for high quality soap, and also used for producing medical and pharmaceutical preparations such as ointment, suppository and medically lubricating agent.

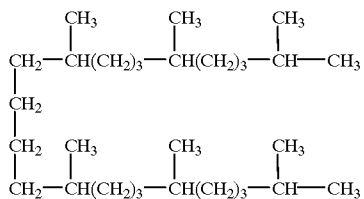

Furthermore, owing to its advantageous properties, it is used as a fiber treating agent, leather surface modifying agent, sizing agent, and face wiping cloth. Still further, in view of its good durability at low temperatures and at high temperatures, it is also used as a lubricating oil for engines and so forth.

As described above, squalane is often used for various purposes. However, it sometimes comes into question when it is brought into contact with the skin, for example, in cosmetics and medical agents, because the pristane which is contained in squalane prepared from shark-liver oil, is stimulative to the skin.

The pristane (2,6,10,14-tetramethylpentadecane) is a saturated hydrocarbon which is represented by a molecular formula of $C_{19}H_{40}$, and which is contained in animal oil or fat such as deep-sea shark-liver oil or else. The terms fat and oil are distinguished by their physical state. The fat is solid at ambient temperature, where the oil is liquid.

In the conventional art, the content of pristane in the commercially available squalane prepared from shark-liver oil is about 1,000 to 2,000 wt ppm.

The art to prepare squalane which does not contain pristane is disclosed in Japanese Laid-Open Patent Publication No. Hei 7-309785. This method was developed for the preparation of squalane from vegetable oils containing no pristane. Of course, this method cannot be applied to the treatment of animal oil.

The production of squalane from vegetable is small. In addition, the content of squalene as a raw material for squalane is also small, so that many processes are required for separation and concentration so as to obtain squalene. Furthermore, after the production of squalene, much waste must be discarded which causes the problem in environmental pollution.

It is considered that the anxiety to cause the disorder with the stimulation to the skin may be practically small when the quantity of pristane is so small as in the ordinary squalane prepared from shark-liver oil. However, the trend to demand a possibly safe product is increasing in recent years.

Accordingly, it is demanded to prepare squalene scarcely containing pristane from shark-liver oil as a raw material.

It is pointed out in recent years that silicone oil which is usually employed as a lubricant for condoms, is injurious to the human health. As a substitute for the silicone oil, the use of squalane is proposed in Japanese Laid-Open Patent Publication No. Hei 9-164162.

The quantity of pristane contained in the products of squalane is on the level that it causes almost no problem concerning the skin of healthy persons. However, because condoms are used in contact with the sensible mucous membrane, it is considered that a minute quantity of pristane may react upon the mucous membrane and it gives rise to undesirable influence of the lowering of sensibility for the mucous membrane. Furthermore, with some physical constitution of a user, there is anxiety that the user feels a pain when he suffers injuries in his mucous membrane.

Therefore, medical lubricating agent of squalane scarcely containing pristane is demanded.

In recent years, the symptom of arthritis caused by adjuvant composition has come into question and squalane is used for the adjuvant composition in place of liquid paraffin.

Examples of the uses of squalene or squalane for adjuvant compositions are disclosed in U.S. Pat. No. 5,718,904 and European Patent 0 399 843 A2. It is disclosed in these patent gazettes that squalane emulsified with an emulsifying agent was used as adjuvant, however, the pristane in the squalane was not investigated.

In recent years, there is a tendency to keep off the application of silicone oil to injection needles because the silicone oil is difficultly excreted by metabolism. It is thus proposed to use squalane in place of the former one (Japanese Laid-Open Patent Publication No. Hei 9-140790).

However, there is no instance to give consideration to the stimulative pristane.

As described above, squalane prepared from animal oil such as shark-liver oil scarcely containing pristane is demanded. It is also required that the quantity of pristane is not more than 10 wt ppm. However, this is difficultly attained through the ordinary distillation because the decomposition or other reaction takes place.

BRIEF SUMMARY OF THE INVENTION

It is, therefore, the primary object of the present invention to provide highly pure squalane scarcely containing pristane which is prepared from animal oils such as shark-liver oil, the raw material of pharmaceuticals and cosmetics using the same and method for preparing the same.

Pursuant to the above objects, the inventors have carried out extensive investigation. As a result, they found that pristane can be effectively eliminated by applying a specific treatment to squalane containing pristane, thereby accomplishing the present invention.

Therefore, a first aspect of the present invention relates to highly pure squalane of animal oil origin which contains not more than 10 wt ppm of pristane.

A second aspect of the present invention relates to the use of the highly pure squalane of the first aspect as a raw material for preparing cosmetics.

A third aspect of the present invention relates to the use of the highly pure squalane of the first aspect as a raw material for preparing medical and pharmaceutical products.

A fourth aspect of the present invention relates to a lubricating agent composed of the highly pure squalane of the third aspect.

A fifth aspect of the present invention relates to condoms applied with the lubricating agent of the fourth aspect.

A sixth aspect of the present invention relates to an adjuvant composition containing the highly pure squalane of the third aspect.

A seventh aspect of the present invention relates to the adjuvant composition of the sixth aspect, wherein the composition comprises 100 wt % in total of:

(a) squalane containing not more than 10 wt ppm of pristane, (b) an emulsifying agent, and (c) an aqueous medium; and the sum of (a) squalane and (b) emulsifying agent is 0.1 to 50 wt % and the quantity of (b) emulsifying agent is 0.1 to 50 wt parts relative to 100 parts by weight of (a) squalane.

An eighth aspect of the present invention relates to the adjuvant composition of the seventh aspect, wherein the diameter of oil particles containing (a) squalane and (b) emulsifying agent is not larger than 1,000 nm.

A ninth aspect of the present invention relates to injection needles to be used for human bodies or animal bodies, which injection needles are applied with the highly pure squalane of the first aspect.

A tenth aspect of the present invention relates to a method for producing highly pure squalane, wherein the content of pristane is reduced to 10 wt ppm or less by means of thin film distillation.

An eleventh aspect of the present invention relates to a method for producing highly pure squalane of the tenth aspect, wherein said thin film distillation is carried out at a pressure of 0.1 mm Hg or lower and a temperature in the range of 100 to 200° C.

DETAILED DESCRIPTION OF THE INVENTION

The present invention will be described in more detail.

The highly pure squalane is prepared by hydrogenating squalene which is obtained from shark-liver oil such as animal oil of deep-sea sharks and then subjecting the hydrogenation product to thin film distillation. The deep-sea sharks are exemplified by *Centrophorus atromarginatus* German, *Centroscymnus owstoni* German, *Deania eglantia* Jordan et Snyder, and *Centroscyllium ritteri* Jordan et Flowler.

The squalene as the raw material used in the present invention can be produced in any means from the shark-liver oil. An example of the preparation of squalene will be described.

Oil and fat content is collected from the liver of shark and the shark-liver oil is obtained by, for example, centrifugal separation. If necessary, the shark-liver oil is filtered and it is subjected to distillation, e.g. vacuum distillation in order to eliminate low temperature components and high temperature components. The thus obtained distillate (hereinafter referred to as "squalene fraction". The squalane fraction is an oily substance containing other components of esters and fatty acids.

The squalane fraction is then subjected to alkali treatment to saponify esters. After that, the reaction products are rinsed with water and dehydrated to obtain squalene scarcely containing esters and fatty acids.

In the next step, the above squalene is hydrogenated to obtain squalane.

The squalene sometimes contains unsaturated hydrocarbons which are corresponding to the pristane. When these unsaturated hydrocarbons are hydrogenated, they are converted into pristane. Even when pristane is removed from squalene before the hydrogenation, there is possibility that pristane is newly produced during the hydrogenation. Accordingly, the elimination of pristane must be done after the hydrogenation.

The catalyst used in the hydrogenation is any one of a single element, sulfide or chloride of platinum, nickel and titanium. These catalysts may be used in the forms of suspension in a reaction mixture or carrier-supported catalyst. As the catalyst carriers, well known ones such as alumina, silica-alumina, activated carbon and magnesia are used. The forms of carrier-supported catalysts are not limited, which are exemplified by any particles of pellets, granules, spheres and extruded rods. They can be selected in accordance with the conditions of hydrogenation.

The conditions for the hydrogenation are the same as those in the conventional art. That is, the temperature is in the range of an ordinary temperature to 300° C., preferably 50 to 300° C.; and the hydrogen pressure is in the range of normal pressure to 200 kg/cm$^2$G, preferably 5 to 150 kg/cm$^2$. The catalytic reaction can be carried out with a fixed bed, suspension bed, moving bed or expansion bed. Furthermore, the reaction system may be any of batch wise and continuous.

It is possible to add a solvent to squalene in the hydrogenation, which solvent is inert to the reaction and can easily be separated from squalane, such as saturated hydrocarbons of n-hexane, isooctane and so forth.

The purity of squalene in the preparation of squalane is higher than about 95 wt %, preferably higher than 98 wt %.

After the hydrogenation, the highly pure squalane is obtained from the obtained squalane by removing impurities such as pristane through thin film distillation.

The thin film distillation employed in the method of the present invention is a kind of refining method, in which a thin film of material is formed with heating under high vacuum to evaporate pristane, thereby separating pristane from the squalane to raise the purity of squalane. In this thin film distillation, the remained non-evaporated squalane is recovered with removing the pristane. So that, for the purpose to carry out the thin film distillation hereinafter referred to, a thin film distillation apparatus, thin film evaporator or the like can be employed.

The manner for forming the thin film is not limited. However, it is preferable that the thin film is forcedly formed by utilizing centrifugal force or shear force with a wiper or blade. In the method to flow down squalane by gravitation, it is necessary to take care of the difficulty in the formation of thin film. The thickness of the thin film is not especially limited, however, it is generally less than 5 mm, preferably less than 3 mm.

The thin film distillation is characterized in that the operation can be done at a low temperature to avoid the decomposition and deterioration of squalane and what is more, the treatment can be done quickly, so that the possibility of decomposition and reaction of squalane is low.

In the present invention, the quantity of pristane can be markedly reduced through the thin film distillation of squalane. It is difficult to attain such removal by means of the ordinary vacuum distillation. Meanwhile, the use of multi-stage distillation column is also difficult because the treating temperature is high. Accordingly, the thin film distillation is considered to be most effective one.

In the method of the present invention, it is possible to remove not only pristane but also other low molecular impurities through the thin film distillation. Accordingly, it is possible to attain the effect not only that pristane is eliminated from squalane but also that the purity of squalane can be improved higher than the level in conventional method.

The usable thin film distillation apparatus are exemplified by Hickman distillation apparatus, falling film evaporator, rotor-tray distillation apparatus, and brush-type molecular distillation apparatus. It is preferable that the distillation is carried out under a pressure of 0.1 mm Hg or below and a temperature of 100 to 200° C. The retention time is not especially limited, however, it is generally not longer than 30 min.

The content of pristane in the thus obtained squalane is not more than 10 wt ppm, preferably less than 5 ppm. More particularly, it is preferable that pristane is not detected substantially. If the content of pristane is more than 10 wt ppm, the quantity of pristane must be reduced to a level below 10 wt ppm by repeating the thin film distillation.

The content of pristane can be determined by the method for determining the purity of product squalane by gas chromatographic analysis according to National Formula of U.S.A.

With the method of the present invention, the purity of squalane can be improved quite easily and promptly by employing the thin film distillation.

The thus obtained squalane is quite suitable as medical, pharmaceutical and cosmetic products and as a raw material for producing them. It is especially suitable as a raw material for producing these products which are brought into contact with skin in use.

The medical and pharmaceutical products are exemplified by cooling agents for burn and scald, several kinds of creams and ointments, poultices, hair tonics, and disinfectants. The cosmetics are exemplified by several kinds of skin nutrient oils, hair ointments, milky lotions, cosmetic creams, lipsticks, cosmetic foundations, eye shadows, and bathing agents.

When squalane is used for these medical, pharmaceutical and cosmetic products, the content of pristane must be very small. In addition, the purity of squalane must be higher than 99 wt %, preferably higher than 99.5 wt %, and more preferably higher than 99.9 wt %.

Concerning medical and pharmaceutical products, the uses for the lubricating agent of condom and for the component of adjuvant composition are especially useful.

It is said that squalane is also generated in the human body. Therefore, no problem may be caused to occur when the above highly pure squalane penetrates into the human body through mucous membrane or wound, because the squalane reacts just as the inherently generated squalane. Therefore, there occurs no problem of the accumulation of squalane. In addition, as the content of pristane is small, it hardly stimulates the skin or mucous membrane. Therefore, it is quite suitable as a lubricant for condom.

As the above-mentioned condoms, any of commonly used ones such as those made of latex rubber can be used. Especially, the lubricating agent according to the present invention is suitably used for condoms made of polyurethane because it is compatible with them.

Condoms made of polyurethane available at present is stronger than those made of latex rubber, however, the former ones are rather stiff. So that, much lubricating agent is required. The hitherto used lubricating agent of silicone oil is not satisfactory in view of lubricating effect. Therefore, a larger quantity of silicone oil must be used. Meanwhile, when the silicone oil is used too much, peculiar uneasy feeling without smooth slipping, the so-called "grating", is caused, which is not desirable.

Furthermore, in the heat-sealing step of packing process, when heat-sealing surface is stained with silicone oil, rejected articles in packing are liable to occur. In the case of the use of squalane, there hardly occurs such an anxiety.

In addition, condoms made of polyurethane are preferred because they have no smell of rubber. The lubricating agent according to the present invention also has no nasty smell, so that the advantage in the combination with condoms made of polyurethane is large in view of odorless.

Still further, condoms made of latex rubber have another disadvantage in that they are swollen when they are soaked into squalane, even though short time soaking can be disregarded. In the case of condoms made of polyurethane, such a problem of swelling is not caused. Also in view of this, the combination of squalane with the polyurethane-made condoms is desirable.

The lubricating agent according to the present invention can be applied to condoms in any arbitrary manner. For example, the lubricating agent may be sprayed to condoms or the latter ones may be immersed into the lubricating agent. It is also possible to apply the lubricating agent to condoms using a brush, or the lubricating agent may be applied to a condom just before the use. It is generally desirable that the lubricating agent is applied to both inner and outer surfaces of condom.

The 0.01 to 20 cc of lubricating agent of the present invention is preferably applied evenly to the whole of a condom.

The adjuvant composition of the present invention is an auxiliary agent to generate antibody and to enhance immunity of cells. Especially, when it is mixed with immunogen, it improves or changes the immune response.

In the present invention, all the well known medicinal agents used generally for adjuvants can be employed as the components besides the highly pure squalane.

The adjuvant composition containing squalane is generally prepared by emulsifying squalane into oil-in-water (O/W) emulsion using an emulsifying agent and it is supplied for use.

When the adjuvant composition is emulsified, an aqueous medium and emulsifying agent are added to prepare emulsion. The aqueous portion of the adjuvant composition may be pure water or buffered saline with phosphates. Because the composition is intended for parenteral administration, it is preferable to make up a final buffered solution so that the tonicity, i.e., osmolarity, is essentially the same as normal physiological fluids in order to prevent post-administration swelling or rapid absorption of the composition because of differential ion concentrations between the composition and physiological fluids. It is also preferable to buffer the saline in order to maintain a pH compatible with normal physiological conditions. Also, in certain instances, it may be necessary to maintain the pH at a particular level in order to insure the stability of certain composition components such as the glycopeptides.

Any physiologically acceptable buffer may be used herein, but phosphate buffers are preferred. Other acceptable buffers such as acetate, tris, bicarbonate, carbonate, or the like may be used as substitutes for phosphate buffers. The pH of the aqueous component will preferably be between 6.0–8.0.

Specific examples of suitable emulsifying agents which can be used in accordance with the present invention include the following:

1. Water-soluble soaps, such as the sodium, potassium, ammonium and alkanol-ammonium salts of higher fatty acids ($C_{10}$–$C_{22}$), particularly sodium and potassium tallow and coconut soaps.

2. Anionic synthetic non-soap detergents, which can be represented by the water-soluble salts of organic sulfuric acid reaction products having in their molecular structure an alkyl radical containing from about 8 to 22 carbon atoms and a radical selected from the group consisting of sulfonic acid and sulfuric acid ester radicals. Examples of these are the sodium or potassium alkyl sulfates, derived from tallow or coconut oil; sodium or potassium alkyl benzene sulfonates; sodium alkyl glyceryl ether sulfonates; sodium coconut oil fatty acid monoglyceride sulfonates and sulfates; sodium or potassium salts of sulfuric acid esters of the reaction product of one mole of a higher fatty alcohol and about 1 to 6 moles of ethylene oxide; sodium or potassium alkyl phenol ethylene oxide ether sulfonates, with 1 to 10 units of ethylene oxide per molecule and in which the alkyl radicals contain from 8 to 12 carbon atoms; the reaction product of fatty acids esterified with isethionic acid and neutralized with sodium hydroxide; sodium or potassium salts of fatty acid amide of a methyl tauride; and sodium and potassium salts of $SO_3$-sulfonated $C_{10}$–$C_{24}$ α-olefins.

3. Nonionic detergents made by the polymerization of alkylene oxide and organic hydrophobic compound. For example, polyoxyethylene, and polyoxyethylene-polyoxypropylene block polymer.

4. Nonionic synthetic detergents made by the condensation of alkylene oxide groups with an organic hydrophobic compound. Typical hydrophobic groups include condensation products of propylene oxide with propylene glycol, alkyl phenols, condensation product of propylene oxide and ethylene diamine, aliphatic alcohols having 8 to 22 carbon atoms, and amides of fatty acids.

5. Nonionic detergents, such as amine oxides, phosphine oxides and sulfoxides, having semipolar characteristics. Specific examples of long chain tertiary amine oxides include dimethyldodecylamine oxide and bis-(2-hydroxyethyl)dodecylamine oxide. Specific examples of phosphine oxides are found in U.S. Pat. No. 3,304,263 (issued Feb. 14, 1967) and include dimethyldodecylphosphine oxide and dimethyl-(2-hydroxydodecyl) phosphine oxide.

6. Long chain sulfoxides, including those corresponding to the formula $R^1$-SO-$R^2$, wherein $R^1$ and $R^2$ are substituted or unsubstituted alkyl radicals, the former $R^1$ containing from about 10 to about 28 carbon atoms, whereas $R^2$ contains from 1 to 3 carbon atoms. Specific examples of these sulfoxides include dodecyl methyl sulfoxide and 3-hydroxy tridecyl methyl sulfoxide.

7. Ampholytic synthetic detergents, such as sodium 3-dodecylaminopropionate and sodium 3-dodecylaminopropane sulfonate.

8. Zwitterionic synthetic detergents, such as 3-(N,N-dimethyl-N-hexadecylammonio)propane-1-sulfonate and 3-(N,N-dimethyl-N-hexadecylammonio)-2-hydroxy propane-1-sulfonate.

Additionally, all of the following types of emulsifying agents can be used in a composition of the present invention:

(a) soaps (i.e., alkali salts) of fatty acids, rosin acids, and tall oil;

(b) alkyl arene sulfonates;

(c) alkyl sulfates, including surfactants with both branched-chain and straight-chain hydrophobic groups, as well as primary and secondary sulfate groups;

(d) sulfates and sulfonates containing an intermediate linkage between the hydrophobic and hydrophilic groups, such as the fatty acylated methyl taurides and the sulfated fatty monoglycerides;

(e) long-chain acid esters of polyethylene glycol, especially the tall oil esters;

(f) polyethylene glycol ethers of alkylphenols;

(g) polyethylene glycol ethers of long-chain alcohols and mercaptans; and (h) fatty acyl diethanol amides.

Since surfactants can be classified in more than one manner, a number of classes of surfactants set forth in this paragraph overlap with previously described surfactant classes.

There are a number of emulsifying agents specifically designed for and commonly used in biological situations. For example, a number of biological detergents (surfactants) are listed as such by Sigma Chemical Company on pages 310–316 of its 1987 Catalog of Biochemical and Organic Compounds. Such surfactants are divided into four basic types: anionic, cationic, zwitterionic, and nonionic.

(i) Examples of anionic detergents include alginic acid, caprylic acid, cholic acid, 1-decanesulfonic acid, deoxycholic acid, 1-dodecanesulfonic acid, N-lauroyl-sarcosine, and taurocholic acid.

(ii) Cationic detergents include dodecyltrimethylammonium bromide, benzalkonium chloride, benzyldimethylhexadecyl ammonium chloride, cetylpyridinium chloride, methylbenzethonium chloride, and 4-picoline dodecyl sulfate.

(iii) Examples of zwitterionic detergents include 3-[(3-cholamidopropyl)-dimethylammonio]-1-propanesulfonate (commonly abbreviated CHAPS), 3-[(cholamidopropyl)-dimethyl-ammonio]-2-hydroxy-1-propanesulfonate (generally abbreviated CHAPSO), N-dodecyl-N,N-dimethyl-3-ammonio-1-propanesulfonate and lyso-α-phosphatidylcholine.

(iv) Examples of nonionic detergents include decanoyl-N-methylglucamide, diethylene glycol monopentyl ether, n-dodecyl-β-D-glucopyranoside, ethylene oxide condensates of fatty alcohols (e.g., trade name: Lubrol), polyoxyethylene ethers of fatty acids (particularly $C_{12}$–$C_{20}$ fatty acids), polyoxyethylene sorbitan fatty acid ethers (e.g., trade name: Tween), and sorbitan fatty acid ethers (e.g., trade name: Span).

A particularly useful group of surfactants are the sorbitan-based non-ionic surfactants. These surfactants are prepared by dehydration of sorbitol to give 1,4-sorbitan which is then reacted with one or more equivalents of a fatty acid. The fatty-acid-substituted moiety may be further reacted with ethylene oxide to give a second group of surfactants.

The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common names for these surfactants include, for example, sorbitan monolaurate, sorbitan monopalmitate, sorbitan monoestearate, sorbitan monooleate, sorbitan sesquioleate, and sorbitan trioleate. These surfactants are commercially available under the name SPAN or ARLACEL, usually with a letter or number designation which distinguishes between the various mono, di- and triester substituted sorbitans.

SPAN and ARLACEL surfactants are hydrophilic and are generally soluble or dispersible in oil. They are also soluble in most organic solvents. In water they are generally insoluble but dispersible. Generally these surfactants will have a hydrophilic-lipophilic balance (HLB) number between 1.8 to 8.6. Such surfactants can be readily made by means known in the art or are commercially available from, for example, ICI America's Inc., Wilmington, Del. under the registered mark: ATLAS.

A related group of surfactants (the second group of nonionic detergents) comprises polyoxyethylene sorbitan monoesters and polyoxyethylene sorbitan triesters. These materials are prepared by addition of ethylene oxide to a 1,4-sorbitan monoester or triester. The addition of polyoxyethylene converts the lipophilic sorbitan mono- or triester surfactant to a hydrophilic surfactant generally soluble or dispersible in water and soluble to varying degrees in organic liquids.

These materials, commercially available under the mark: TWEEN, are useful for preparing oil-in-water emulsions and dispersions, or for the solubilization of oils and making anhydrous ointments water-soluble or washable. The TWEEN surfactants may be combined with a related sorbitan monoester or triester surfactants to promote emulsion stability. TWEEN surfactants generally have a HLB value falling between 9.6 to 16.7.

TWEEN surfactants are commercially available from a number of manufacturers, for example ICI America's Inc., under the registered mark: ATLAS surfactants.

A third group of non-ionic surfactants which could be used alone or in conjunction with SPAN, ARLACEL and TWEEN surfactants are the polyoxyethylene fatty acids made by the reaction of ethylene oxide with a long-chain fatty acid. The most commonly available surfactant of this type is sold under the name MYRJ and is a polyoxyethylene derivative of stearic acid. MYRJ surfactants are hydrophilic and soluble or dispersible in water like TWEEN surfactants.

The MYRJ surfactants may be blended with TWEEN surfactants or with TWEEN/SPAN or ARLACEL surfactant mixtures for use in forming emulsions.

MYRJ surfactants can be made by methods known in the art or are available commercially from ICI America's Inc.

A fourth group of polyoxyethylene based non-ionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ. BRIJ surfactants may be hydrophilic or lipophilic depending on the size of the polyoxyethylene moiety in the surfactant. While the preparation of these compounds is available from the art, they are also readily available from such commercial sources as ICI America's Inc.

Other non-ionic surfactants which could potentially be used in the practice of this invention are for example: polyoxyethylene, polyol fatty acid esters, polyoxy-ethylene ether, polyoxypropylene fatty ethers, bee's wax derivatives containing polyoxyethylene, polyoxyethylene lanolin derivative, polyoxyethylene fatty glycerides, glycerol fatty acid esters or other polyoxyethylene acid alcohol or ether derivatives of long-chain fatty acids of 12–22 carbon atoms.

As the adjuvant according to this invention, it is preferable to choose an emulsion-forming non-ionic surfactant which has an HLB value in the range of about 7 to 16. This value may be obtained through the use of a single non-ionic surfactant such as a TWEEN surfactant or may be achieved by the use of a blend of surfactants such as with a sorbitan mono, di- or triester based surfactant; a sorbitan ester polyoxyethylene fatty acid; a sorbitan ester in combination with a poly-oxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

It is more preferred to use a single non-ionic surfactant, most particularly a TWEEN surfactant, as the emulsifying agent to stabilize the emulsion in the practice of this invention. The surfactant named TWEEN 80, otherwise known as polysorbate 80 for polyoxyethylene sorbitan mono-oleate, is the most preferred of the foregoing surfactants.

In the present invention, the combination of two or more emulsifying agents, i.e. surfactants, can be used.

A adjuvant composition according to the present invention comprises 100 wt % as total of the foregoing squalane, an emulsifying agent and an aqueous medium, in which 0.1 to 50 wt %, preferably 0.3 to 40 wt % and more preferably 0.5 to 30 wt % of the mixture of the above squalane and emulsifying agent.

The content of the emulsifying agent is in the range of 0.1 to 50 wt parts, preferably 0.5 to 45 wt parts, relative to 100 wt parts of squalane.

Any method can be employed for preparing the emulsion of adjuvant composition of the present invention. For example, the emulsification can be attained using e.g. a homogenizer. The size of oily particles is preferably not larger than 1,000 nm, more preferably smaller than 750 nm.

The adjuvant composition according to the present invention can contain, if necessary, terpenoid, vegetable oil and so forth besides the above-described components. Furthermore, the adjuvant composition can contain lecithin, a glycopeptide, glycerides, phospholipid, and glycelol. If necessary, an aluminum compound can also be incorporated.

The adjuvant composition is sometimes used as it stands, however, it is generally used together with an antigen. That is, it is used together with the so-called vaccine or it is used as one component of vaccine.

The vaccines used in the present invention include both inactivated whole and subunit vaccines as well as toxoids. Moreover, the vaccines employed are those used to immunize against bacterial, rickettsial and viral pathogens. Suitable human vaccines would include for example, the whole and subunit vaccines for influenza, poliomyelites, arbovirsus infections, typhoid and paratyphoid, ekolcra, plague, pertussis, typhus, Rocky Mountain Spotted Fever, Haemophilus influenza type B, multivalent pneumococcal polysaccharid, and meningococcal group C., tixoids, and the newly developed human diploid cell rabies vaccines and hepatitus vaccine.

Suitable veterinary vaccines would include, for example, the whole and subunit vaccines for equine influenza viruses, equine herpesviruses, equine encephalomyelitis viruses, wart virus, foot-and-mouth disease virus, rabies, feline panleukopenia, feline rhinotracheitis, feline calicivirus, infectious bovine rhinotracheitis, para-influenza-3, bovine virus diarrhea, bovine adenoviruses, pseudorabies, transmissible gastroenteritis virus, porcine parvovirus, canine adenoviruses, canine distemper virus and canine parainfluenza. Whole and subunit vaccines, bacterins and toxoids for strangles, brucellosis, vibriosis, leptospirosis, clostridial infections, salmonellosis, colibacillosis, anaplasmosis, pasteurella infections, haemophilus infections, erysipelothrix and the like.

According to the present invention, the above whole vaccines, subunit vaccines and toxoids are used by any one of them to the adjuvant composition or they can be used separately.

The injection needles for human bodies or animal bodies herein referred to are those in which at least the tip end portions of the injection needles are applied or coated with the highly pure squalane according to the present invention. The types of injection needles are not limited as far as they are used for the injection to human bodies or animal bodies. They are usually made of a metal such as stainless steel. In the present invention, the quantity of application of highly pure squalane may not be limited as far as it is effective. In a typical instance, the squalane in the range of 0.0003 to 10,000 $\mu$g is applied to a unit area (1 mm$^2$) of the tip end portion of injection needle.

The tip end portion herein referred to means the range of 5 to 20 mm from the needle point. As occasion demands, when there is no problem, the highly pure squalane can be applied to other part of injection needle of as well as to the tip end portion.

The method for applying highly pure squalane to the tip end portion of injection needle is not especially limited. For example, injection needles are soaked in highly pure squalane, the needles are sprayed with the highly pure squalane or the needles are brought into contact with cotton wool that is impregnated with the highly pure squalane so as to apply the squalane to injection needles.

In the application of highly pure squalane to the injection needles of the present invention, it is also possible to apply the highly pure squalane by diluting it with an appropriate organic solvent, which is followed by the removal of volatile components from the surfaces of the injection needles.

Furthermore, it is also possible that an anti-oxidizing agent such as vitamin E or lecithin is added to the highly pure squalane, if it is desirable.

EXAMPLES

In the following passage, the present invention will be described in more detail.

Method for Analysis

The purity of squalene and the quantity of pristane were determined according to the foregoing NF method. The conditions for the gas chromatographic analysis were as follows:

| | |
|---|---|
| Detector | Hydrogen flame ion detector (FID) |
| Column | 3 mm (in. dia.) × 2 m (l) |
| Stationary phase carrier | 80/100 mesh, |
| Trade name: UNIPORT HP, | made by GL Science Co., Ltd. |
| Carried liquid phase: | 3% carried, |
| Trade name: SE-30, | made by GL Science Co., Ltd. |
| Injection temp. | 350° C. |
| Carrier gas: helium, flow rate | 60 ml/min |
| Hydrogen pressure | 1.0 kg/cm$^2$ |
| Air pressure | 1.0 kg/cm$^2$ |
| Feed | 2.0 $\mu$l |
| Preparation of sample | 2 ml of sample was dissolved into 50 ml of n-hexane |

Highly Pure Squalane

<Example 1>

(Step 1)

The light components and heavy components were removed from 2,000 g of deep-sea shark-liver oil (squalene content: 70.5 wt %, imported from Europe) using a stainless steel distillation column to obtain 1,380 g of squalene fraction as a main fraction of 175–180° C. (0.5 mm Hg).

(Step 2)

The squalene fraction obtained in Step 1 was saponified, which was followed by warm water rinsing. More particularly, 100 wt parts of the squalene fraction and 32 wt parts of 40 wt % sodium hydroxide aqueous solution were fed into a reaction vessel equipped with a stirrer to carry out the saponification at 85° C. for 5 hours. After that, the oily phase was rinsed 5 times with warm water and it was confirmed that the oil phase was not alkaline. The obtained squalene was then warmed under reduced pressure to remove dissolved water and the treated squalene was subjected to hydrogenation. Its properties are shown in the following.

Purity of squalene: 99.0 wt %

Content of pristane: 1500 wt ppm (Step 3)

A material for hydrogenation was prepared by dissolving 10 wt parts of squalene obtained in Step 2 into 90 wt parts of n-hexane.

A tubular reactor of 1.2 cm in inner diameter and 10 cm in length was packed with 10 g of carrier-supported nickel catalyst. Hydrogenation was carried out by feeding into the reactor the n-hexane solution of squalene and hydrogen gas to obtain a squalane solution in n-hexane. Samples were taken out for 30 hours after the temperature was stabilized at 200° C.

The conditions for the hydrogenation were as follows:

Flow rate of squalene solution in n-hexane: 30 ml/hr

Flow rate of hydrogen gas: 2.5 Nl/hr

Reaction temperature: 200° C.

Pressure of hydrogen gas: 60 kg/cm$^2$G (Step 4)

Using an evaporator, n-hexane was removed from the squalane solution in n-hexane obtained in the above Step 3. Using then a centrifugal thin film distillation apparatus, light components were removed with a feed rate of 15 kg/hr and at a temperature of 150° C. and a pressure of 0.03 mm Hg to obtain highly pure squalane.

The properties of the thus obtained highly pure squalane were as follows:

Purity of squalane: Not lower than 99.9 wt %

Content of pristane: Not detected

<Example 2>

(Step 1)

The light components and heavy components were removed from 2,000 g of deep-sea shark-liver oil (squalene content: 71.0 wt %, sulfur content: 24 wt ppm, obtained from Philippines) using a rotary evaporator to obtain 1,290 g of the main squalene fraction of 175–180° C. (at 0.5 mm Hg).

(Step 2)

The squalene fraction obtained in Step 1 was saponified, which was followed by warm water rinsing. More particularly, 100 wt parts of the squalene fraction and 27 wt parts of 30 wt % sodium hydroxide aqueous solution were fed into a reaction vessel equipped with a stirrer to carry out the saponification at 80° C. for 6 hours with stirring.

After separating the aqueous phase from the oily phase, the oily phase was rinsed with warm water at 50° C. until rinsing waste water became pH 7. The dissolved water in the obtained squalene was then removed at 75° C. under a pressure of 30 mm Hg. The treated squalene was subjected to hydrogenation. Its properties are shown in the following.

Purity of squalene: 99.6 wt %

Content of pristane: 1300 wt ppm (Step 3)

A material for hydrogenation was prepared by dissolving 50 wt parts of squalene obtained in Step 2 into 50 wt parts of isooctane.

A tubular reactor of 2.0 cm in inner diameter and 10 cm in length was packed with 20 g of carrier-supported nickel catalyst. Hydrogenation was carried out by feeding into the reactor the 50 wt % squalene solution in isooctane and hydrogen gas to obtain a squalane solution in isooctane. Samples were taken out for 30 hours after the temperature was stabilized at 210° C.

The conditions for the hydrogenation were as follows:

Flow rate of squalene solution in isooctane: 30 ml/hr

Flow rate of hydrogen gas: 5.2 Nl/hr

Reaction temperature: 210° C.

Pressure of hydrogen gas: 60 kg/cm$^2$G (Step 4)

Using an evaporator, isooctane was removed from the squalane solution in isooctane obtained in the above Step 3. Using then the same centrifugal thin film distillation apparatus as the one used in Example 1, light components were removed with a feed rate of 15 kg/hr and at a temperature of 145° C. and a pressure of 0.01 mm Hg to obtain highly pure squalane.

The properties of the thus obtained highly pure squalane were as follows:

Purity of squalane: Not lower than 99.9 wt %

Content of pristane: Not detected

<Example 3>

The test was carried out in the like manner as in Example 1 except that the tubular reactor used in Step 3 of Example 1 was changed to another one of 2.0 cm in inner diameter and 10 cm in length and that the flow rate of squalene solution in n-hexane was 620 ml/hr and the flow rate of hydrogen gas was 10 Nl/hr.

The properties of the thus obtained highly pure squalane were as follows:

Purity of squalane: 99.0 wt %

Content of pristane: 3 wt ppm

<Example 4>

The test was carried out in the like manner as in Example 2 except Step 3. In Step 3, hydrogenation was done batch-wise using a 2 liter stainless steel autoclave with a stirrer. The used catalyst was made in the manner such that the catalyst used in Example I was finely crushed into a particle size of 150 mesh through.

The conditions for the hydrogenation were as follows:

| Duration of reaction | 3 hr |
|---|---|
| Reaction temperature | Hydrogenation was started at 130° C. and, after that, the temperature was maintained at 200° C. |
| Quantity of catalyst | 0.75 g |
| Quantity of squalene solution in isooctane | 1,000 g |
| Pressure of hydrogen gas | 70 kg/cm$^2$G |

The properties of the thus obtained highly pure squalane were as follows:

Purity of squalane: 99.9 wt %

Content of pristane: Not detected

<Example 5>

The test was carried out in the like manner as in Example 1 except Step 3. In Step 3, hydrogenation was done batch-wise using a 2 liter stainless steel autoclave with a stirrer. The used catalyst was made in the manner such that the catalyst used in Example 1 was finely crushed into a particle size of 150 mesh through.

The conditions for the hydrogenation were as follows:

| Duration of reaction | 3 hr |
|---|---|
| Reaction temperature | Hydrogenation was started at 130° C. and, after that, the temperature was maintained at 200° C. |
| Quantity of catalyst | 1.5 g |
| Quantity of squalene | 200 g (Solvent was not used |
| Pressure of hydrogen gas | 70 kg/cm$^2$G |

The properties of the thus obtained highly pure squalane were as follows:

Purity of squalane: 99.9 wt %

Content of pristane: Not detected

<Comparative Example 1>

Test was carried out in the like manner as in Example 1 except that the thin film distillation was not done.

The properties of the thus obtained squalane were as follows:

Purity of squalane: Not lower than 98.5 wt %

Content of pristane: 1,400 wt ppm

<Example 6>

Squalane was prepared from commercially available shark-liver oil (purity of squalane: 99.6 wt %, quantity of pristane: 150 wt ppm). This squalane was subjected to vacuum distillation and light components were then removed by thin film distillation at 1500° C. and 0.05 mm Hg.

The properties of the thus obtained squalane were as follows:

Purity of squalane: 99.9 wt %

Content of pristane: Not detected

Cosmetic Product

<Example 7>

The highly pure squalane obtained in Example 1 was emulsified and it was used as a raw material for preparing a cosmetic cream. The quality of the obtained cream was quite desirable.

Medical and Pharmaceutical Product
<Example 8>

The highly pure squalane obtained in Example 1 was cooled to −60° C. and it was applied to burned mice. As a result, conspicuous effect was observed.

Condom
<Example 9>

The squalane obtained in Example 1 was applied to condoms made of polyether urethane rubber on positive molds. After that, the condoms were wound up and they were used for evaluation. The results are shown in the following Table 1.

The evaluation was done by the test panel of 10 persons. (This will be applied to the following examples.)
<Example 10>

The condoms made of polyether urethane rubber which were wound were immersed into the squalane obtained in Example 1. The results are shown in the following Table 1.
<Example 11>

The squalane obtained in Example 2 was applied to condoms made of polyether urethane rubber on positive molds. After that, the condoms were wound up and they were used for evaluation. The results are shown in the following Table 1.
<Example 12>

The condoms made of polyether urethane rubber which were wound were immersed into the squalane obtained in Example 2. The results are shown in the following Table 1.
<Comparative Example 2>

A commercially available squalane having the following properties was applied to condoms made of polyether urethane rubber on positive molds. After that, the condoms were wound up and they were used for evaluation. The results are shown in the following Table 1.

Purity of squalane: 99.5 wt %

Content of pristane: 1,479 wt ppm
<Reference Example>

A commercially available dimethyl silicone for cosmetic use was applied to condoms made of polyether urethane rubber on positive molds. After that, the condoms were wound up and they were used for evaluation. The results are shown in the following Table 1.

TABLE 1

| | Feeling in Wearing | | | |
|---|---|---|---|---|
| | Good (Score) | Not Good (Score)* | Slippery Property | Squeaking Feeling |
| Example 9 | 10 | 0 | Good | None |
| Example 10 | 10 | 0 | Good | None |
| Example 11 | 10 | 0 | Good | None |
| Example 12 | 9 | 1 | Good | None |
| Comparative Example 2 | 6 | 4 | Regular | None |
| Reference Example | 4 | 6 | Slightly Worse | Recognized |

Note:
Score: The number of panel members

It was understood not only that the quantity of pristane is small but also that all the condoms in Examples of this invention had slippery property with smooth feeling without stickiness and they had agreeable touch feeling, as compared with the samples in Comparative Example and Reference Example.

Adjuvant Composition
<Example 13>

(Preparation Method)

The adjuvants of this invention may be produced by the following steps:

(1) All the components for adjuvant compositions (aqueous buffer, highly pure pristane and other components prepared in Example 1) should first be brought to a temperature of about 37° C.

(2) The above components were mixed together and were allowed to come to room temperature. This mixture should be held at room temperature for about 15 minutes.

(3) The emulsifying agent is then added to the mixture, with mixing. This total mixture of adjuvant components can then be autoclaved and sonicated to create a sterile, homogeneous emulsion. Sonication was done in an ice bath for 5 minutes, which was followed by 15 seconds gaps of holding the adjuvant mixture on ice. After this sonic treatment, the average size of emulsion particles was 220 nm.

The emulsions prepared through the above procedure were used as adjuvant compositions. The formations of obtained adjuvant compositions were as follows:

Adjuvant No. 1: Composition containing 5% highly pure squalane, 1% lecithin and 0.2% TWEEN 80.

Adjuvant No. 2: Composition containing 5% highly pure squalane, 1% glycerol and 0.2% TWEEN 80.

The remainder parts of the above adjuvant compositions were phosphate buffer.

(Evaluation)

Adjuvant compositions of this invention were prepared as above and mixed with trivalent Wyeth-Ayerst 1993 influenza virus vaccine, which is described on page 2578 of the 1993 Physician's Desk Reference, 47th Edition.

1.5 µg of the hemagglutinin of each of the three strains present in the vaccine, A/Beijing/32/92, A/Texas/36/91 and B/Panama/45/90, were given to groups of 6 female, 7-week old CD-1 mice. Each mouse received intramuscular injections of 0.2 ml of the above vaccine. At 28 days following inoculation, the mice were bled and the serum assayed by the hemagglutination inhibition procedure (HI test) for antibodies to the A/Beijing component.

The geometric mean average titer of the 6 mice in each group was as follows:

Adjuvant No. 1: HI titer 2055

Adjuvant No. 2: HI titer 2126

Injection Needle
<Example 14>

Sterilized cotton wool was impregnated with the highly pure squalane obtained in Example 1 and intramuscular injection needles were penetrated into the soaked cotton wool, thereby applying the squalane to the needles.

Using the above squalane-treated injection needles and untreated injection needles, comparison tests were done concerning the stinging pain and the bleeding in the use of injection needles. In the tests, ten parsons were pricked with the respective two kinds of needles. The results of the tests are shown in the following Table 2.

TABLE 2

| | Needles treated with highly pure squalane | Untreated needles |
|---|---|---|
| Number of persons who felt stronger stinging pain | 1 | 9 |
| Number of persons with whom more bleeding was observed | 3 | 7 |

As described above, according to the present invention, it is possible to prepare squalane from animal oils or fats such as shark-liver oil, which squalane is not stimulative to the skin and of less deterioration by light rays or heat because the content of pristane is quite small.

Accordingly, the squalane proposed in the present invention is advantageously used as raw materials for preparing cosmetics, medical and pharmaceutical products, household utensils, food additives, fiber treating agents, lubricating agents, heating or cooling medium, coating agents, anti-corrosive agent, and so forth.

Furthermore, because the quantity of impurities is not so large which is different from the conventional squalane, the problem in the reaction between impurities and other additional components can be disregarded.

Still further, as compared with the lubricating agents and condoms prepared by using the same in the conventional art, those prepared according to the present invention are low in stimulation to the skin and have lubricating effect and moistening effect.

It is said that squalane has activating effect for cellular tissues, antiphlogistic effect and activating effect for sex hormones, so that the lubricating agent of the present invention is quite suitable for condoms.

The adjuvant composition of the present invention can be used quite safely as compared with those in the prior art because the purity of squalane in the present invention is very high.

What is claimed is:

1. Highly pure squalane containing not more than 10 ppm by weight of pristane, wherein said squalane is of animal oil or animal fat origin.
2. A cosmetic product comprising the highly pure squalene as claimed in claim 1.
3. A medical or a pharmaceutical product comprising the highly pure squalane as claimed in claim 1.
4. A lubricating agent for condoms which agent comprises the highly pure squalane as claimed in claim 1.
5. An adjuvant composition which contains the highly pure squalane as claimed in claim 1.
6. The adjuvant composition as claimed in claim 5 wherein said composition comprises 100 wt % in total of:
   (a) squalane containing not more than 10 wt ppm of pristane,
   (b) an emulsifying agent, and
   (c) an aqueous medium; and
   the sum of (a) squalane and (b) emulsifying agent is 0.1 to 50 wt % and the quantity of (b) emulsifying agent is 0.1 to 50 wt parts relative to 100 parts by weight of (a) squalane.
7. The adjuvant composition as claimed in claim 6, wherein the diameter of oily particles containing (a) squalane and (b) emulsifying agent is not larger than 1,000 nm.
8. A method for producing highly pure squalane comprising reducing the content of pristane in squalane by means of thin film distillation, wherein the amount of the pristane in said highly pure squalane is 10 ppm by weight or less, and wherein said squalane is of animal oil or animal fat origin.
9. The method for producing highly pure squalane as claimed in claim 8, wherein said thin film distillation is carried out at a pressure of 0.1 mm Hg or lower and a temperature in the range of 100 to 200° C.
10. A method as claimed in claim 8, wherein the squalane subjected to said thin film distillation is obtained by hydrogenation of squalene obtained from animal oil.
11. A method as claimed in claim 10, wherein said hydrogenation of the squalene is conducted in the presence of an inert solvent.
12. A method as claimed in claim 11, wherein said thin film distillation is conducted at a temperature from 80° C. to 200° C., and a pressure of 0.1 mm Hg or below.
13. A highly pure squalane as claimed in claim 1, containing less than 5 ppm by weight of pristane.
14. A highly pure squalane as claimed in claim 1 wherein said squalane is of shark liver oil origin.
15. An adjuvant composition as claimed in claim 6, wherein said emulsifying agent is selected from biological surfactants selected from anionic, cationic, nonionic, and zwitterionic surfactants or combinations thereof.
16. An adjuvant composition as claimed in claim 14, wherein said emulsifying agent is at least one nonionic surfactant having an HLB value from about 7 to about 16.
17. An adjuvant composition as claimed in claim 15 wherein said squalane is of shark liver oil origin.
18. A method as claimed in claim 10 wherein said squalane is of shark liver oil origin.

* * * * *